US006645232B2

(12) United States Patent
Carson

(10) Patent No.: US 6,645,232 B2
(45) Date of Patent: Nov. 11, 2003

(54) PATIENT TEMPERATURE CONTROL SYSTEM WITH FLUID PRESSURE MAINTENANCE

(75) Inventor: Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 39 days.

(21) Appl. No.: 09/976,198

(22) Filed: Oct. 11, 2001

(65) Prior Publication Data

US 2003/0078639 A1 Apr. 24, 2003

Related U.S. Application Data

(63) Continuation-in-part of application No. 09/476,850, filed on Jan. 3, 2000, now Pat. No. 6,375,674, which is a continuation-in-part of application No. 09/225,070, filed on Jan. 4, 1999, now Pat. No. 6,197,045.

(51) Int. Cl.[7] .................................................. A61F 7/00
(52) U.S. Cl. ....................................... 607/104; 607/108
(58) Field of Search ........................... 607/96, 104–112; 219/506

(56) References Cited

U.S. PATENT DOCUMENTS

| | | | |
|---|---|---|---|
| 3,007,473 A | | 11/1961 | Jackson |
| 3,064,649 A | | 11/1962 | Fuson |
| 3,074,410 A | | 1/1963 | Foster |
| 3,460,538 A | | 8/1969 | Armstrong |
| 3,504,674 A | | 4/1970 | Swenson et al. |
| 3,625,279 A | | 12/1971 | Mayo et al. |
| 3,888,259 A | | 6/1975 | Miley |
| 3,894,213 A | * | 7/1975 | Agarwala ................... 392/471 |
| 3,995,621 A | | 12/1976 | Fletcher et al. |
| 4,149,529 A | * | 4/1979 | Copeland et al. ............. 601/17 |
| T994,001 I4 | | 5/1980 | Buckberg et al. |
| 4,259,961 A | | 4/1981 | Hood, III |
| 4,416,280 A | | 11/1983 | Carpenter et al. |
| 4,427,009 A | | 1/1984 | Wells et al. |
| 4,459,468 A | * | 7/1984 | Bailey ......................... 219/490 |

(List continued on next page.)

Primary Examiner—Roy D. Gibson
(74) Attorney, Agent, or Firm—Marsh Fischmann & Breyfogle LLP

(57) ABSTRACT

An improved patient temperature exchange system and method is disclosed for use with one or more interconnectable patient contact pads. In one embodiment, the system includes a circulating pump for drawing fluid through the interconnected pad(s) under negative pressure, and for pumping the fluid through one of more heat exchange devices into a circulating reservoir. A make-up reservoir may be provided for gravity fluid flow into the circulating reservoir during the filling of the interconnectable pad(s) and for receiving fluid upon emptying of the interconnectable pad(s). During normal heating/cooling operations, the circulated fluid does not pass through the make-up reservoir, thereby yielding a highly responsive system. The make-up and circulatory reservoirs may be directly interconnected, with the make-up reservoir maintained at atmospheric pressure (e.g. via a non-spill vent). To reliably maintain the desired negative pressure in the interconnectable pad(s), the system may provide for fluid pressure sensing on the inlet side of the circulating pump. The sensed pressure may be utilized to control the speed of the circulating pump. The system may further provide for the positioning of pressure drop a componentry on the outlet side of the circulating pump, thereby further facilitating the maintenance of a desired negative pressure within the interconnected pad(s). A bypass fluid line may also be included to provide for fluid preconditioning prior to interconnection of and/or fluid flow through the pad(s). Multiple temperature sensors and an interface for an external patient temperature input may also be provided for enhanced fluid heating/cooling control.

20 Claims, 8 Drawing Sheets

U.S. PATENT DOCUMENTS

| | | | |
|---|---|---|---|
| 4,508,123 A | | 4/1985 | Wyatt et al. |
| 4,512,163 A | | 4/1985 | Wells et al. |
| 4,523,594 A | | 6/1985 | Kuznetz |
| 4,691,762 A | * | 9/1987 | Elkins et al. ............... 165/46 |
| 4,844,072 A | | 7/1989 | French et al. |
| 4,962,761 A | | 10/1990 | Golden ....................... 128/400 |
| 4,966,145 A | | 10/1990 | Kikumoto et al. |
| 5,033,136 A | * | 7/1991 | Elkins ........................... 5/421 |
| 5,051,562 A | * | 9/1991 | Bailey et al. ............... 219/506 |
| 5,097,778 A | | 3/1992 | Quisenberry |
| 5,266,778 A | | 11/1993 | Bailey |
| 5,270,005 A | | 12/1993 | Raible |
| 5,332,884 A | | 7/1994 | Bailey |
| 5,466,216 A | | 11/1995 | Brown et al. |
| 5,573,502 A | | 11/1996 | LeCocq et al. |
| 5,634,940 A | | 6/1997 | Panyard |
| 5,733,320 A | | 3/1998 | Augustine |
| 5,862,675 A | | 1/1999 | Scaringe et al. |
| 5,865,841 A | | 2/1999 | Kolen et al. ................. 607/104 |
| 5,871,526 A | | 2/1999 | Gibbs et al. |
| 5,895,418 A | * | 4/1999 | Saringer ..................... 607/104 |
| 36,386 | | 11/1999 | Abbott et al. |
| 5,980,561 A | | 11/1999 | Kolen et al. |
| 5,989,285 A | | 11/1999 | DeVilbiss et al. |
| 6,033,432 A | | 3/2000 | Augustine et al. |
| 6,086,609 A | * | 7/2000 | Buckley ....................... 604/26 |
| 6,095,992 A | | 8/2000 | Augustine |
| 6,149,674 A | | 11/2000 | Borders |
| 6,197,045 B1 | | 3/2001 | Carson |

\* cited by examiner

PATIENT TEMPERATURE CONTROL SYSTEM WITH FLUID PRESSURE MAINTENANCE

RELATED APPLICATION

This application is a continuation-in-part and claims priority from U.S. patent application Ser. No. 09/476,850, filed Jan. 3, 2000, and issued as U.S. Pat. No. 6,375,674 on Apr. 23, 2002, which is a continuation-in-part and claims priority from U.S. patent application Ser. No. 09/225,070, filed Jan. 4, 1999, and issued as U.S. Pat. No. 6,197,045, on Mar. 6, 2001.

FIELD OF THE INVENTION

The present invention relates to the selective raising and/or lowering of patient temperatures, and more particularly, to systems and methods for controlling a patient's temperature via the circulation of heated/cooled fluid through one or more pads contacting a patient.

BACKGROUND OF THE INVENTION

The use of contact pad systems for selectively cooling and/or heating bodily tissue is known. In such systems a fluid, e.g. water or air, is circulated through one or more pads to affect surface-to-surface thermal energy exchange with a patient. One highly effective contact pad and related system is disclosed in U.S. Pat. No. 6,197,045, hereby incorporated by reference in its entirety. As noted in the '045 patent, the ability to establish and maintain intimate pad-to-patient contact is often of key importance to fully realizing medical efficacies with contact pad systems.

In this later regard, the effect of temperature on the human body has been well documented. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Temperature management, or thermoregulation, can be viewed in two different ways. The first aspect of temperature management includes treating abnormal body temperatures, i.e. cooling the body for elevated temperatures, or warming the body for lowered temperatures. The second aspect of thermoregulation is an evolving treatment that employs techniques that physically control a patient's temperature to provide a physiological benefit, such as cooling a stroke patient to gain some degree of neuroprotection.

Hypothermia may occur for a variety of reasons, including exposure to cold environments, brain injury, or complex surgical procedures. During surgery, a patient typically experiences mild hypothermia as a result of the effect of general anesthesia on the body's thermoregulatory system and prolonged exposure of internal organs. Mild hypothermia in the medical or the surgical patient has been thought to prolong the time to extubation, contribute to coagulopathies, increase the chance of infection, and increase cardiac demand as a result of shivering.

Hyperthermia may occur as a result of systemic inflammatory response, sepsis, stroke, or other brain injury. While the mechanism of the effect of the hyperthermia on the brain is not clearly understood, there is evidence to indicate that even mild increases in temperature may contribute to neurological deficits. Hyperthermia also increases the metabolic rate and may deplete energy stores in the body.

In view of the foregoing, it may be appreciated that recognized medical applications for contact pad systems are ever-increasing. By way of example, cooling pad systems may be utilized in early therapy to reduce neurological damage incurred by stroke and head trauma patients. Additional applications include selective patient heating/cooling during surgical procedures such as cardiopulmonary bypass operations.

As these and other medical applications have evolved, the present inventors have recognized the desirability of enhancing the predictability, responsivity, flexibility and portability of thermal exchange pad systems. More particularly, while known heating/cooling contact pad systems have proven effective for many applications, the present inventors have recognized that additional performance objectives and potential applications can be realized via the implementation of further improved control systems and associated control methodologies.

SUMMARY OF THE INVENTION

In particular, one objective of the present invention is to provide an improved patient temperature control system and method that provides rapid heating/cooling capabilities via one or more interconnectable contact pads while also yielding size, weight and operating efficiencies.

Another objective of the present invention is to provide an improved patient temperature control system and method that offers high thermal exchange reliability while accommodating application flexibility via the interconnectability of either one or a plurality of contact pads.

An additional objective of the present invention is to provide an improved patient temperature control system and method that facilitates ready set-up and portability.

A further objective of the present invention is to provide an improved patient temperature control system that yields enhanced wear and performance of one or more interconnectable contact pads.

Yet a further objective of the present invention is to provide an improved patient temperature control system and method that enhances patient comfort.

One or more of the above objectives and additional advantages may be realized by utilizing the temperature control system features and associated methods disclosed hereinbelow. The system features may include at least one heat exchanger for affecting at least one of heating and cooling a fluid, a circulating pump for circulating the fluid through the heat exchanger, and at least one interconnectable patient contact pad to affect heat transfer therebetween. For purposes hereof, the term "contact pad" refers to any type of pad through which fluid may be flowed from an input port to an output port and which is otherwise adapted to contact a patient to affect heating or cooling.

In one aspect, the inventive system may also include at least a first fluid reservoir, or "make-up fluid reservoir", fluidly interconnectable with the contact pad(s). The first fluid reservoir may be utilized to contain fluid that is removable from the reservoir to fill/circulate through the pad(s) during use. In conjunction with this aspect, the system may be defined so that, during normal heating/cooling operations, fluid is circulatable through the pad(s) and the heat exchanger(s) by the circulating pump substantially free from passage through the first fluid reservoir. By virtue of this arrangement, rapid fluid temperature changes may be achieved in the system since only the circulated fluid is temperature controlled (e.g., not any additional fluid remaining within the first fluid reservoir during fluid circulation). Relatedly, reduced heat exchanger requirements may be realized. Further, flexibility may be maintained by containing a fluid volume in the first reservoir that is sufficient for filling a plurality of interconnectable contact pads.

Preferably, the system also comprises a second fluid reservoir, or "circulating fluid reservoir", through which fluid is circulated during normal heating/cooling operations. In that regard, the first and second reservoirs may be directly, fluidly interconnected so that fluid may be removed from and flowed back into the first fluid reservoir via passage through the second fluid reservoir. Further, the heat exchanger, circulating pump and first and second fluid reservoirs may be supportably located within a common housing, wherein the system is substantially self-contained to facilitate portable use.

More particularly, all or at least a portion of the first fluid reservoir may be physically located above the second fluid reservoir to provide for gravity fluid flow from the first reservoir to the second reservoir. Relatedly, the top of the first reservoir may be maintained at substantially atmospheric pressure (e.g. via a vent having a semi-permeable filter), wherein gas may be removed from/passed into the system. Further, a sensor may be provided at the second fluid reservoir for sensing the amount of fluid contained by the second reservoir, wherein a user output may be provided if/when the fluid amount drops below a predetermined amount.

For example, the sensor may provide an output signal to a controller (e.g. a microprocessor), wherein the controller transmits a signal to a user out put (e.g. a display and/or audible output device). Such user output may not only alert a user of the condition but may also advise the user regarding fluid refilling procedures. Further, the controller may automatically turn-off the circulating pump and heat exchanger if/when the sensed fluid amount in the reservoir drops below a predetermined level.

In further relation to the above-noted aspect, the first fluid reservoir and second fluid reservoir may be provided to contain first and second fluid volumes, respectively, of the fluid present within the system (e.g. when the system is fluidly disconnected from the interconnectable pads), wherein the first fluid volume is greater than the second fluid volume. Preferably, the first fluid volume is between about 3% and 50% of the first fluid volume. As may be appreciated, the interconnectable contact pad(s) may have an internal volume greater than the second fluid volume, wherein at least some of the fluid contained in the first fluid reservoir may be flowed out of the first reservoir for circulation through the pad(s) during heating/cooling. The amount of fluid removed from the first reservoir for such purpose(s) will depend on the number of pads that are interconnected.

In conjunction with the foregoing, it may appreciated that an inventive temperature control method is provided that includes the steps of containing a fluid in a first fluid reservoir and flowing at least a portion of that fluid out of the first reservoir, wherein the removed portion is circulated through at least one interconnected contact pad and a heat exchanger fluidly interconnected therewith, substantially free passage through the first reservoir. In turn, the method further comprises the step of contacting the pad(s) to a patient to affect heat transfer therebetween. Typically, an amount of fluid corresponding with the removed portion is returned to the first fluid reservoir, e.g. upon completion of a given patient heating/cooling procedure.

The method may further include the step of selectively establishing the fluid interconnection of the contact pad(s). In this regard, it is contemplated that the method may be practiced utilizing a system that may be selectively and readily interconnected to and disconnected from one or a plurality of contact pads, as deemed appropriate by medical personnel for heating/cooling a patient in a given situation. For such purposes, the method may further provide for holding a first fluid volume in the first fluid reservoir and a second fluid volume in a second fluid reservoir, wherein the first and second fluid volumes are combinatively sufficient to fill a plurality of contact pads. Preferably, the amount of fluid present in the second fluid reservoir may be sensed, wherein a sensor output signal is employable to provide a user output (e.g. when the fluid level drops below a preset amount), as noted above.

The described system and method may also provide for drawing the circulated fluid through the interconnectable contact pad(s) under negative pressure. Such negative pressure may be established by locating the circulating pump downstream of the pad(s), wherein fluid is pumped out of the pad(s) and then through the heat exchanger into the second fluid reservoir. As noted, the second fluid reservoir may be maintained at substantially atmospheric pressure. Preferably, the inventive method may further provide for locating the interconnected contact pad(s) above the first and second fluid reservoirs. Such location facilitates fluid flow out of the interconnectable contact pad(s) and back into the system, e.g. in the event of pad leakage/pump stoppage.

In another aspect, an inventive temperature patient control system is provided which includes not only a circulating pump and at least one heat exchanger, but additionally a pressure sensor fluidly interconnected between an inlet side of the circulating pump and an outlet port of the interconnectable contact pad(s). The pressure sensor may provide an output pressure signal employable to control the circulating pump. Again, the circulating pump may be disposed to establish a negative pressure in the interconnectable contact pad. In turn, the output pressure signal may be employed to control the circulating pump so as to maintain the negative pressure within a predetermined range. Such an arrangement facilitates the maintenance of a desired minimum pressure in each of the one or more interconnectable contact pads.

Additionally, the system may include a controller for receiving the output pressure signal from the pressure sensor and for providing a control signal to the circulating pump in response thereto. In the later regard, the control signal may be provided to control the operating speed of the pump. More particularly, the controller may utilize the outlet pressure signal and a predetermined information set (e.g. corresponding with a desired pressure range for the interconnectable contact pad(s)) to control the operating speed of the pump.

The inventive system may also include a flow meter for measuring a flow rate of the fluid between an outlet side of the circulating pump and an inlet port of the interconnectable contact pad(s), wherein the flow meter provides an output flow signal. In turn, a user output device may be included to provide an output in response to the identification of a predetermined relationship between the output flow signal and the pump operating speed and/or the output pressure signal. By way of primary example, such predetermined relationship may correspond with conditions which may indicate the presence of a potential fluid circuit blockage (e.g. a kink in a tubing line used for pad interconnection). The user output may include remedial action information to assist a user in addressing the situation.

In the described system, the flow meter and heat exchanger(s), as well as any other pressure-drop system components (e.g. fluid reservoir(s)) may be preferably located downstream of the circulating pump and upstream of the interconnectable pad(s). By so doing, the desired negative pressure in the interconnectable pads may be more reliably maintained. Again, the noted system components may be supportably disposed in a common housing to yield a self-contained system.

In conjunction with the inventive system noted above, it may be appreciated that a patient temperature control method is provided that includes the steps of operating a circulating pump to circulate a fluid through a heat exchanger and at least one interconnected contact pad, and sensing a pressure of the fluid between an inlet side of the circulating pump and an outlet port of the at least one interconnected contact pad, wherein the sensed fluid pressure is employed in the pump operating step. The operating step may provide for the establishment of a negative pressure in the contact pad(s). Further, an output pressure signal may be provided in relation to the sensed pressure, wherein the output pressure signal is employed in the operating step to maintain the negative pressure within a predetermined range. Such predetermined range may be set in relation to the attributes of the given interconnected contact pad(s) so as to insure a minimum fluid flow sufficient to affect the desired heat transfer while avoiding high pressures that could unduly stress the contact pad(s).

The inventive method may further include the steps of containing at least the portion of the circulated fluid in a fluid reservoir, and maintaining the fluid reservoir at substantially atmospheric pressure. In turn, the maintaining step may provide for a venting of the fluid reservoir, e.g. to the ambient atmosphere.

Additionally, the method may include the step of utilizing the above-noted output pressure signal to provide a control signal to the circulating pump (e.g. via a microprocessor controller), wherein such control signal controls an operating speed of the pump. Further, the method may include the step of measuring a flow rate downstream of the circulating pump and upstream of the inlet port of the interconnected contact pad(s), wherein an output flow signal may be provided (e.g. to controller). In turn, the method may provide a user output in response to the identification of a predetermined relationship between the output flow signal and the pump operating speed and/or the output pressure signal. As noted, such predetermined relationship may be established in relation to conditions which would indicate a blockage in the fluid circuit of the system. The user output may be provided to identify at least one remedial response that may be undertaken by a user.

In an additional aspect, an inventive system is provided that includes a heat exchanger for at least one of heating/cooling a fluid, a circulating pump for circulating a fluid through the heat exchanger and an interconnectable contact pad, and a fluid reservoir which is fluidly interconnectable with the interconnectable pad(s) and which contains at least a portion of the circulated fluid. Of importance to this aspect, the fluid reservoir is internally maintained at substantially atmospheric pressure. For such purposes a vent may be interconnected to the fluid reservoir, such vent having a porous, hydrophobic membrane to permit gas passage and restrict fluid passage therethrough. Further, the circulating pump may be disposed to establish a negative pressure in the interconnectable pad(s). Such an arrangement facilitates reliable fluid passage through the contact pad(s) and minimizes fluid leakage in the event the pad(s) is punctured or otherwise breached.

A vent line may also be provided between the noted vent (e.g. at the fluid reservoir) and an outlet side of the fluid reservoir. Further, a vent valve may be provided for opening and closing the vent line, wherein upon opening the vent line gas is free to pass through the vent line and the interconnectable contact pad(s) in response to the negative pressure established therewithin. Preferably, the vent line is interconnected to a top end of the fluid reservoir.

For purposes of opening/closing the vent valve a controller may also be provided. Relatedly, a user interface may be included for receiving user input instructions for operation of the controller. That is, for example, a user may operate the system in one mode of operation in which the vent valve is closed and fluid is circulated through the interconnectable contact pad(s). In another mode of operation the controller may be "instructed" to open the vent valve so that gas is drawn through the at least one interconnectable contact pad(s) to purge fluid therefrom. Such mode of operation may be utilized at the completion of a given patient temperature control procedure. Again, the various system components may be supportably disposed in a common housing.

In view of the foregoing, a further inventive method is also provided that includes the steps of operating a circulating pump to circulate fluid through a heat exchanger, a fluid reservoir and at least one contact pad fluidly interconnected therewith, and maintaining the fluid reservoir at substantially atmospheric pressure. The operating step may provide for the establishment of a negative pressure in the interconnected contact pad. Relatedly, the contact pad(s) may be preferably located above the fluid reservoir.

To purge fluid from the interconnected contact pad(s) the method may further provide for the flowing of a gas though a vent line and into the interconnected contact pad. Such gas flow may be selectively achieved by the opening/closing of a vent valve disposed in the vent line in response to control signals provided by a controller. Again, such control signals may be provided in response to input instructions provided by a user, wherein fluid may be purged in one mode of operation and circulated for heating/cooling in another mode of operation.

In yet a further aspect, a patient temperature control system and method are provided that utilize a heat exchanger, a circulating pump for circulating fluid through the heat exchanger and an interconnectable pad(s), and a fluid bypass line for flowing the fluid from an outlet side of the heat exchanger back to an inlet side of the circulating pump. Such an arrangement allows for the heating/cooling of the circulated fluid free from passage through an interconnectable contact pad(s), e.g. to achieve fluid preconditioning prior to interconnection of or fluid flow through the pad(s). In conjunction with this inventive system/method, a bypass valve may be employed for opening and closing the fluid bypass line. Further, a controller may be provided for supplying control signals to open/close the valve. In turn, the system/method may also utilize a user interface for receiving instructions at the controller, e.g. commands to initiate/terminate fluid conditioning thereby causing the bypass valve to be opened/closed.

In one arrangement, the inventive system may also comprise a fluid reservoir for containing at least a portion of the circulated fluid, wherein the fluid bypass line extends between the fluid reservoir and the inlet side of the circulating pump. Such reservoir may be vented for removing gas from the system as noted above.

Further, a fluid temperature sensor may be utilized for sensing the temperature of the circulated fluid and providing an output temperature signal in response thereto. In turn, such output temperature signal may be utilized in the control of the heat exchanger. For example, a controller may receive the fluid output temperature signal to control the operation of the heat exchanger, wherein the fluid is adjusted to a temperature within a predetermined range. Such range may be set at the user interface noted above. Again the noted system components may be supportably disposed in a common housing.

In yet a further aspect, a patient temperature control system and method are provided that utilize first and second heat exchangers for heating and cooling a fluid, respectively, and a circulating pump for circulating fluid through at least one interconnectable contact pad. A housing is also provided to supportably house the pump and first and second heat exchangers, wherein one of the heat exchangers is selectively interconnectable to an external source for providing one of a heating or cooling medium. By virtue of the noted arrangement, a temperature control system and associated method may be provided with reduced componentry and weight, thereby enhancing affordability. By way of primary example, one of the noted heat exchangers maybe selectively interconnectable with an external fluid refrigeration system that provides a chilled fluid for applications requiring significant fluid cooling.

The inventive system/method may further employ an auxiliary pump for pumping fluid through the heat exchanger that is interconnected with the external source. In turn, a fluid temperature sensor may be provided for sensing the temperature of the system fluid and providing an output temperature signal employable for controlling the operation of the auxiliary pump. In this regard, a controller may also be provided for receiving the output temperature signal and providing a control signal to set the speed of the auxiliary pump, wherein a desired degree of heat transfer with the external source is achieved.

In yet an additional aspect of the present invention, a patient temperature control system and method are provided that utilize a heat exchanger for one of heating and cooling a fluid, a circulating pump for circulating the fluid through the heat exchanger and at least one fluidly interconnectable contact pad, and first and second fluid temperature sensors that are located upstream and downstream, respectively, of the heat exchanger. Such sensors sense the temperature of the circulated fluid and provide first and second temperature output signals. Further, a controller may be employed to utilize the first and second temperature output signals to provide a control signal to the heat exchanger. By virtue of the described arrangement, an amount of heat exchange through the interconnectable contact pad(s) to/from a patient may be determined since the temperature of the fluid flowing to/from the pad(s) is determined. As such, the heat exchanger may be more precisely controlled to achieve targeted patient temperature.

Further in this regard, the system/method may employ a flow meter for measuring a flow-rate of the fluid between the circulating pump and an outlet port to the interconnectable contact pad(s). Such flow meter may provide a flow-rate output signal that is also employable by the controller in the provision of the heat exchanger control signal.

Additionally, the noted system/method may include a controller adapted to receive an input signal indicative of a patient's temperature and to employ such signal in the provision of the heat exchanger control signal. By way of example, the input may signal may be received from one or more patient core temperature sensors. By way of example, such patient core temperature sensor(s) may compare a nasopharynegeal, esophageal, bladder, tympanic and/or rectal probe(s).

As may be appreciated, various ones of the features noted above may be combined in an optional system. Further, numerous user interface features may be implemented to yield a highly automated and user-friendly system.

Additional aspects and advantages of the present invention will become apparent to those skilled in the art upon consideration of the further description provided hereinbelow.

DETAILED DESCRIPTION

FIGS. 1, 2 and 3A–3C relate to one embodiment of a patient temperature control system comprising numerous aspects of the present invention. As will be apparent to those skilled in the art, such aspects may be implemented in various other embodiments.

Figure 1:
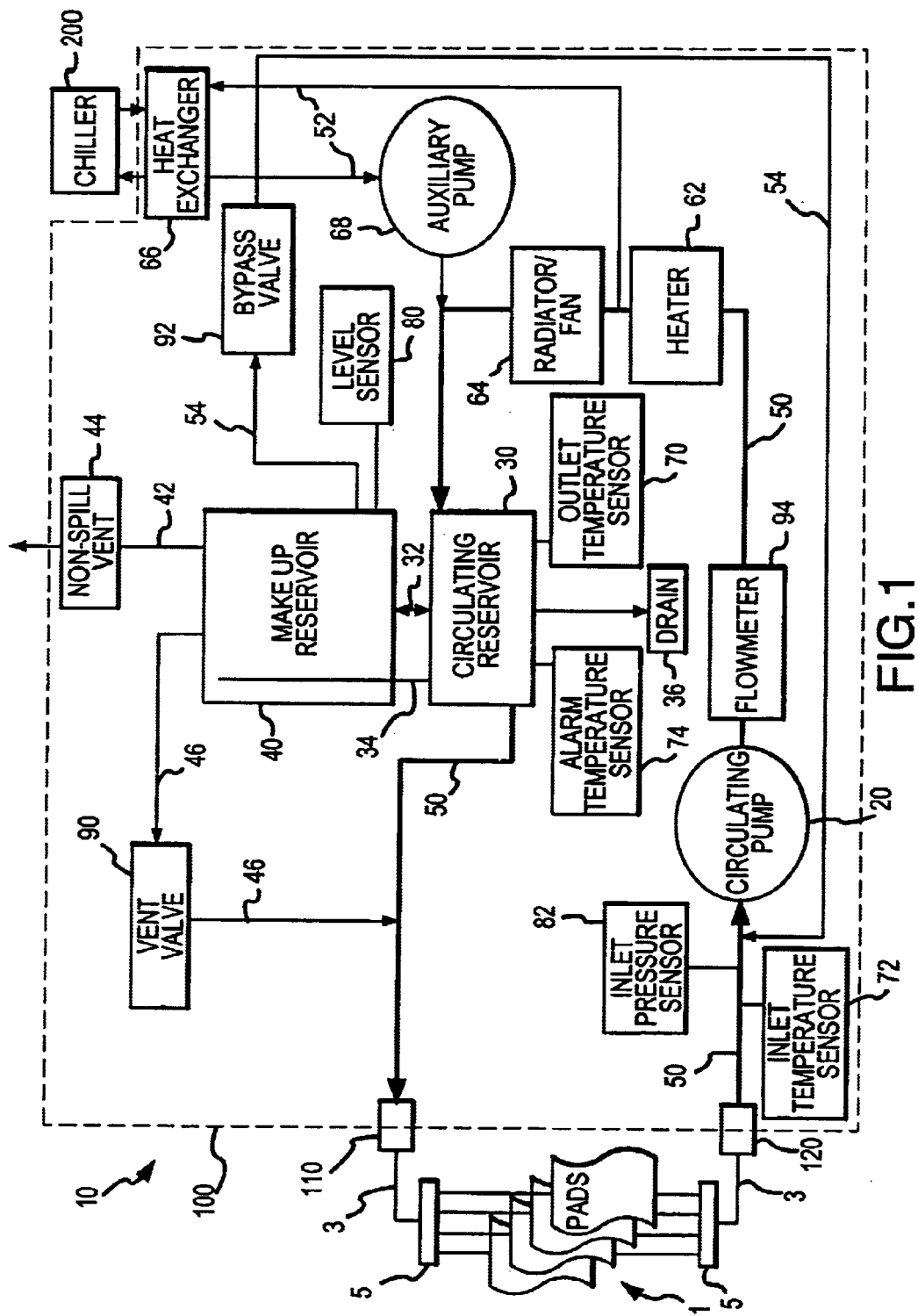
FIG. 1 is a hydraulic schematic of one embodiment of a patient temperature control system comprising numerous aspects of the present invention.

In accordance with the hydraulic schematic of FIG. 1, the illustrated patient temperature control system 10 may be selectively interconnected to one or more contact pad(s) 1 for heating/cooling a patient. By way of example, pad(s) 1 may be of a type described in U.S. Pat. No. 6,197,045. The system 10 includes a circulating pump 20 for drawing fluid (e.g. water) through the pad(s) 1 under negative pressure (e.g. preferably at least about −3 psi, and negative most preferably at least about −7 psi, during normal operations), a circulating reservoir 30 and make-up reservoir 40 for containing fluid, and controllable heat exchange devices 62, 64 (e.g., an electric heater for fluid heating and a radiator/fan for room temperature fluid cooling) for heating/cooling fluid circulated through the system 10.

A main fluid line 50 (e.g., defined by tubing lines) fluidly interconnects the noted system componentry. A secondary fluid line 52 (e.g., defined by tubing lines) may be fluidly interconnected at each end to the main fluid line 50 with an in-line heat exchange device 66 to effect further selective fluid cooling/heating via an external interface. Additionally, a fluid bypass line 54 (e.g. defined by tubing lines) may be fluidly interconnected between reservoir 40 and circulating pump 20 for selective fluid conditioning purposes.

Reservoirs 30 and 40, circulating pump 20, heat exchange devices 62, 64 and 66, and the noted fluid lines 50, 52 and 54, all may be located within a common housing 100.

Housing 100 may be provided with a selectively openable/closeable fluid output port 110 and fluid input port 120 for selective fluid interconnection of the pad(s) 1 therebetween. In the latter regard, opposing tubing 3/manifold 5 assemblies may be provided for interconnection to the outlet port 110 and inlet port 120, with one or more pad(s) 1 fluidly interconnectable between the opposing manifolds 5.

As will be further described, during filling/emptying of the pad(s) 1 (e.g. after fluid conditioning and interconnection of the pad(s) 1), fluid flows from the circulating reservoir 30 into the pad(s) 1 and from/to make-up reservoir 40 to/from circulating reservoir 30. During normal patient heating/cooling operations, fluid is circulated through the circulating reservoir 30, pad(s) 1, and heat exchange devices 62 and 64 and/or 66, substantially free from passage through the make-up reservoir 40.

The fluid containment, handling and heat exchange componentry of system 10 will now be described in further detail with reference to FIGS. 1 and 3A–3C. Circulating reservoir 30 may be physically located below the make-up reservoir 40, with a fluid interconnection line 32 extending therebetween. In the embodiment shown in FIGS. 3A–3C, the top of the circulating reservoir 30 is located below the bottom of the make-up reservoir 40. As will become apparent, such an arrangement provides for the gravity flow of fluid flow from make-up reservoir 40 into circulating reservoir 30. Relatedly make-up reservoir 40 may be physically located lower than pad(s) 1 when interconnected.

During operation, gas within circulating reservoir 30 may rise through fluid interconnection line 32 into the make-up reservoir 40. Further, a vent line 34 may be provided at the top of circulating reservoir 30 for gas removal therefrom. Vent line 34 may be vented through a non-spill outlet to the atmosphere or, as shown in FIG. 1, may be vented into the make-up reservoir 40. In turn, make-up reservoir 40 may be provided with a vent line 42 having a non-spill outlet 44 to the atmosphere. Vent 44 functions to maintain atmospheric pressure (e.g. about 14.7 psi) within the make-up reservoir 40. By way of example, vent 44 may comprise a porous hydrophobic membrane that restricts fluid flow and permits gas passage therethrough.

As may be appreciated, the inclusion of vent lines 34 and 42 advantageously provides for the removal of gaseous bubbles from the fluid circulated through pad(s) 1. In this regard, it should be noted that if a leak develops in the fluid circuit located outside of system 10 (e.g., a leak in the pad(s) 1), air will be drawn through the leak into the system 10 due to the negative pressure operating condition generated by circulating pump 20. In turn, such air will ultimately be exhausted from make-up reservoir 40 via the non-spill vent 44.

For purposes of emptying fluid from the pad(s) 1, the system 10 may include a vent line 46 interconnected at one end to the main fluid line 50 downstream of the circulating reservoir 30. The other end of vent line 46 may be interconnected to the top of make-up reservoir 40. A controllable vent valve 90 may be interposed along the vent line 46 at a physical location above the make-up reservoir 40 to provide for selective gas flow therethrough. More particularly, to empty the pad(s) 1, vent valve 90 may be selectively opened while circulating pump 20 is operating. In turn, air will be drawn through the vent 44, make-up reservoir 40, and vent valve 90 into the main fluid line 50 for passage through and purging of fluid within the pad(s) 1. At the same time, the fluid within the pad(s) 1 will be drawn therefrom by circulating pump 20 and thereafter collected in the make-up reservoir 40 via passage through the circulating reservoir 30.

Fluid may be removed from the system 10 via a drain 36 fluidly interconnected to and located below the circulating reservoir 30. When the pad(s) 1 are disconnected from the system 10, fluid may be readily introduced into the system 10 via the outlet port 110.

The heat exchange devices 62, 64 and 66 may all be located downstream of the circulating pump 20 and upstream of the circulating reservoir 30. Such positioning isolates the pressure drop associated with these components to the positive pressure side of circulating pump 20, thereby enhancing the ability of pump 20 to maintain the desired negative pressure within the pad(s) 1.

As further illustrated in FIG. 1, a separately controllable auxiliary pump 68 may be interposed along the secondary fluid line 52 for selectively circulating fluid through the heat exchange device 66. The heat exchanger device 66 may be disposed at a location within housing 100 that facilitates convenient interconnection with an external cooling and/or heating source. In one arrangement, the heat exchange device 66 may comprise a two-sided exchanger located in the bottom of housing 100, wherein fluid is circulated from an external chiller 200 through one side of the heat exchanger 66 and back through the chiller 200, wherein fluid within system 10 is passed through the other side of the heat exchanger 66 for enhanced cooling purposes. The speed of auxiliary pump 68 may be selectively controlled to affect the desired degree of fluid cooling/heating at exchanger 66. The provision of a secondary fluid line 52 as described above allows large and heavy refrigeration or heating equipment to be utilized in combination with system 10, yet be physically separated from system 10. This results in a significantly smaller and lighter system 10, enhancing portability.

With further respect to fluid bypass line 54, FIG. 1 shows the fluid interconnection thereof between make-up reservoir 40 and main fluid line 50 at a location upstream of circulating pump 20 and downstream from the pad(s) 1. The fluid bypass line 54 is routed through a controllable bypass valve 92, wherein fluid flow through the fluid bypass line 54 may be selectively controlled. In particular, bypass valve 92 may be opened to provide for the preconditioning of fluid in the system 10 prior to interconnection of the pad(s) 1. For example, fluid may be circulated through the bypass fluid line 54 via operation of circulating pump 20 and heat exchange devices 62, 64 and/or 66, thereby achieving the desired fluid temperature prior to interconnection of the pad(s) 1. In turn, effective patient temperature control can be more rapidly established and patient comfort may be enhanced.

In addition to the above-described fluid routing, containment and heat exchange componentry, the system 10 illustrated in FIGS. 1, 2 and 3A–3C also comprises a number of sensors for system control and enhanced performance purposes. In particular, a level sensor 80 may be provided at make-up reservoir 40 for sensing the amount of fluid therewithin. In one arrangement, level sensor 80 may comprise a pressure sensor, wherein the amount of fluid within reservoir 40 may be determined in relation to the sensed head pressure. Such fluid level sensing may be employed in system 10 to provide for user alert, system control and/or system disablement upon sensing of fluid levels below and/or above predetermined amounts.

For purposes of establishing the desired temperature of fluid circulated through the pad(s) 1, system 10 may utilize one or more temperature sensors. In particular, an outlet temperature sensor 70 may be located along the main fluid line 50 at a location downstream of the heat exchange devices 62, 64 and 66. In the embodiment illustrated in FIG. 1, the outlet temperature sensor 70 is provided at the circulating reservoir 30 for sensing the fluid temperature therewithin. Alternatively and/or additionally, an inlet temperature sensor 72 may be located along the main fluid line 50 at a location downstream of the pad(s) 1 and upstream from the heat exchange devices 62, 64 and 66. In the embodiment illustrated in FIG. 1, the inlet temperature sensor 72 is located upstream from the circulating pump 20. The fluid temperature sensed by sensors 70 and/or 72 may be utilized in connection with the control of one or more of the heat exchange devices 62, 64 and 66 (e.g. by controlling operation of auxiliary pump 68), to obtain the desired temperature for fluid circulation. As will be further described, the inclusion of both an outlet fluid temperature sensor 70 and inlet temperature sensor 72 advantageously allows for the ongoing computation of the rate of thermal energy exchange between the pad(s) 1 and a given patient, thereby yielding information employable for enhanced system performance. (e.g. control of the heat exchange devices 62, 64 and pump 68 to rapidly ramp to within a predetermined range of a "targeted" patient temperature).

In addition to temperature sensors 70 and 72, system 10 may further include an alarm fluid temperature sensor 74 located along the main fluid line 50 downstream from the heat exchange devices 62, 64, and 66. In the embodiment illustrated in FIG. 1, the alarm temperature sensor 74 is located at the circulating reservoir 30 for sensing the fluid temperature therewithin. The alarm temperature sensor 74 provides for temperature sensing that may be redundant to that of outlet temperature sensor 70, wherein any risk of circulating fluid outside of a predetermined temperature range may be substantially reduced. For example, system 10 may be provided so that upon the sensing of a fluid temperature outside of a predetermined high/low range, by either of the sensors 70 or 74, circulating pump 20 is automatically stopped.

System 10 may further include an inlet pressure sensor 82 located downstream of the interconnectable pad(s) 1 and upstream of the circulating pump 20. More particularly, the inlet pressure sensor 82 may be located along the main fluid line 50 between the inlet port 120 and inlet side of circulating pump 20. The sensing of fluid pressure at the noted location facilitates the maintenance of a predetermined, desired negative pressure within the interconnectable pad(s) 1. In this regard, the speed of the circulating pump 20 may be controlled in relation to the sensed fluid pressure at sensor 82. Such functionality is provided by the described arrangement regardless of whether one or a plurality of pad(s) 1 are interconnected to the system 10.

System 10 may also include a flow meter 94 located along the main fluid line 50 downstream of circulating pump 20. In the illustrated embodiment, the flow meter 94 is located between the circulating pump 20 and heat exchange devices 62, 64 and 66. The flow meter 94 provides for the sensing of fluid flow through the main fluid line 50, thereby facilitating the monitoring of expected versus actual fluid flow through the pad(s) 1. In turn, such functionality allows system 10 to detect potential, undesired fluid flow obstructions (e.g., kinks in the tubing lines 3 interconnecting the pad(s) 1 to the inlet port 110 or outlet port 120). Additionally, the monitoring of fluid flow rates facilitates the determination of patient thermal energy exchange and fluid heating/cooling control.

As indicated above, the various heat exchange devices 62, 64 and 66, pumps 20 and 68, and valves 90 and 92 may all be selectively controlled. As also noted, the identified sensors may provide information employable to achieve a number of system control functions. To further describe such functionalities, specific reference will now be made to the electrical schematic of FIG. 2. Of importance, system 10 may include at least one controller, or microprocessor 130, operably interconnected to the various noted sensors via a signal-conditioning interface 140. By way of example, the signal conditioning interface 140 may comprise hardware/software for filtering, shifting, etc. of analog signals received from the various sensors. Further, an AID converter may be provided at interface 140 or processor 130 to convert the conditioned signals into digital signals for processing.

As will be appreciated, the processor 130 may be preprogrammed to process the digital signals to provide the various control functionalities discussed herein. More particularly, the processor 130 may utilize control algorithms and associated preset/user-defined control limits/ranges stored in a memory 132 (e.g., a non-volatile random access memory). For purposes of selectively modifying certain control limit sets employable with the control algorithms, as well as initiating/terminating certain system operations, system 10 may include a user interface 150 interconnected with processor 130. The user interface 150 may include one or more input devices (e.g., a keypad entry, touch screen, mouse with a pointer, etc.), as well as one or more displays 152. The displays 152 may display system operating conditions, settings and alarms to a user and/or prompt a user in the set-up and operation of system 10, as well as remedial actions that may be undertaken in the event of a detected system condition of concern.

At this point, it should be noted that system 10 may further include or be interconnectable with a power source 160 (e.g., 24-volt DC source) that powers an internal drive circuit (not shown). In turn, the drive circuit may supply drive signals to the various sensors noted above, as well as a temperature simulator 180, calibration simulator 182 and control chip 172. Additionally, power source 160 may provide drive signals via a switch 162 to the vent valve 90, bypass valve 92, circulating pump 20, and auxiliary pump 68, and to heater 62 via a solid state relay 164 (SSR). Finally, power source 160 may provide drive signals directly to radiator/fan 64 and an electronics fan 170.

While power source 160 supplies drive signals to each of the above-noted fluid handling and heat exchange devices, processor 130 controls the operation thereof. More particularly, processor 130 may control the open/close state of vent valve 90 and bypass valve 92. Processor 130 may also control the operation (e.g., the speed) of circulating pump 20 and auxiliary pump 68. Further, processor 130 can control the operation of heater 62 and radiator/fan 64 (e.g., via control of the fan) to effect the desired amount of heating and cooling. In the embodiment shown in FIG. 2, a relay 166 is interposed between the processor 130 and auxiliary pump 68 and radiator/fan 64, wherein control signals from processor 130 will be directed to radiator/fan 64 when an external heat exchange device 200 is not utilized, and wherein control signals from processor 130 are directed to auxiliary pump 68 when an external heat exchange device 200 is interconnected. In other arrangements, control signals may be provided in tandem to both radiator/fan 64 and auxiliary pump 68 for dual operation thereof.

Figure 2:
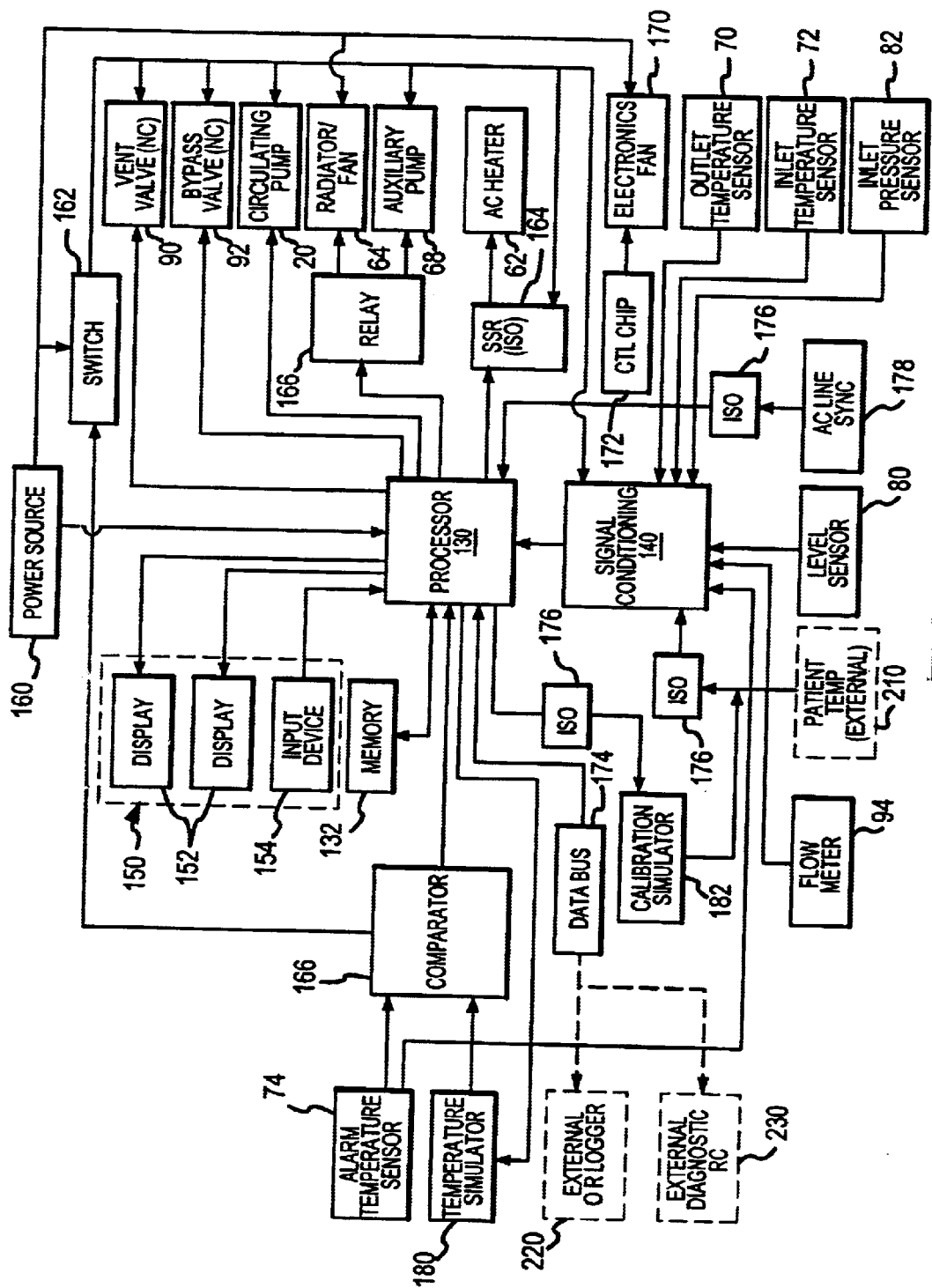
FIG. 2 is an electrical schematic corresponding with the embodiment of FIG. 1.
Figure 3A:
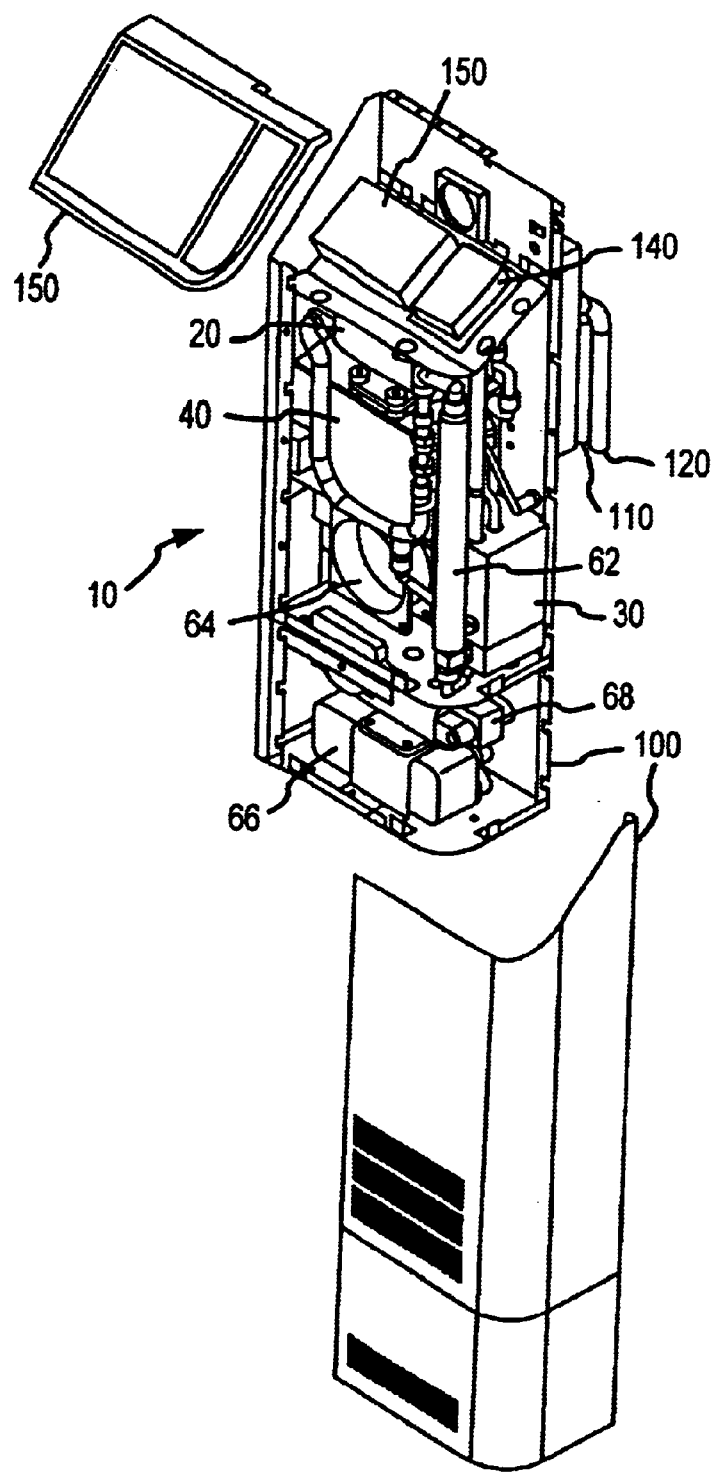
FIGS. 3A, 3B and 3C are an exploded perspective view, a front view and a side view, respectively, of the embodiment of FIG. 1.
Figure 3B:
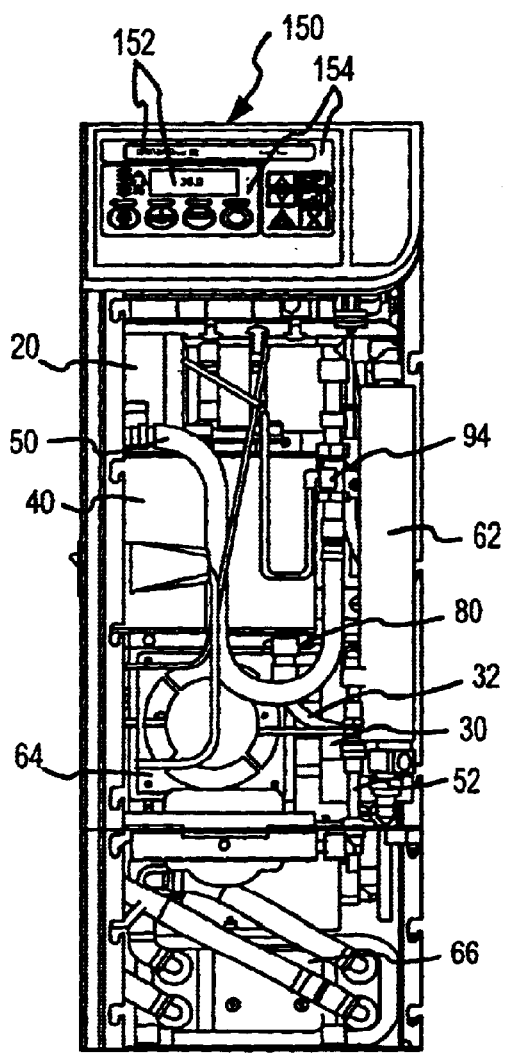
Figure 3C:
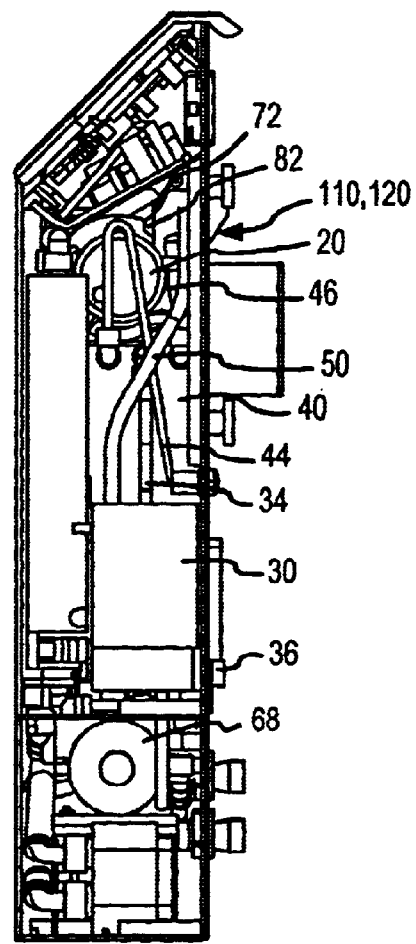

Of note, FIG. 2 illustrates the interconnection of one or more external patient temperature sensors 210 with the signal conditioning interface 140. Patient temperature sensor(s) 210 may comprise, for example, one or more bodily core temperature sensors (e.g. nasopharynegeal, esophageal, bladder, tympanic and rectal probes) that provide analog signals to the signal conditioning interface 140. In turn, the interface 140 provides digital signals to processor 130 for use in the application of preset temperature control algorithms. By way of primary example, the temperature data received from external sensor(s) 210 may be utilized at processor 130 to determine the amount and rate of thermal exchange to be affected by the system 10 in relation to preset/user-defined patient "target" temperatures. In turn, processor 130 may provide the appropriate control drive signals to heater 62, radiator/fan 64 and/or auxiliary pump 68.

In addition to the components, FIG. 2 also illustrates that an external operating room data logger 220 and/or an external diagnostic processor 230 may be selectively interconnected via a data bus 174 to the processor 130. As will be appreciated, the ability to interface system 10 with logger 220 and/or processor 230 allows for the downloading and uploading of digital information, including information collected from one or more of the sensors of system 10 or digital information utilized in the processing of and response to the sensor information.

Figure 4:
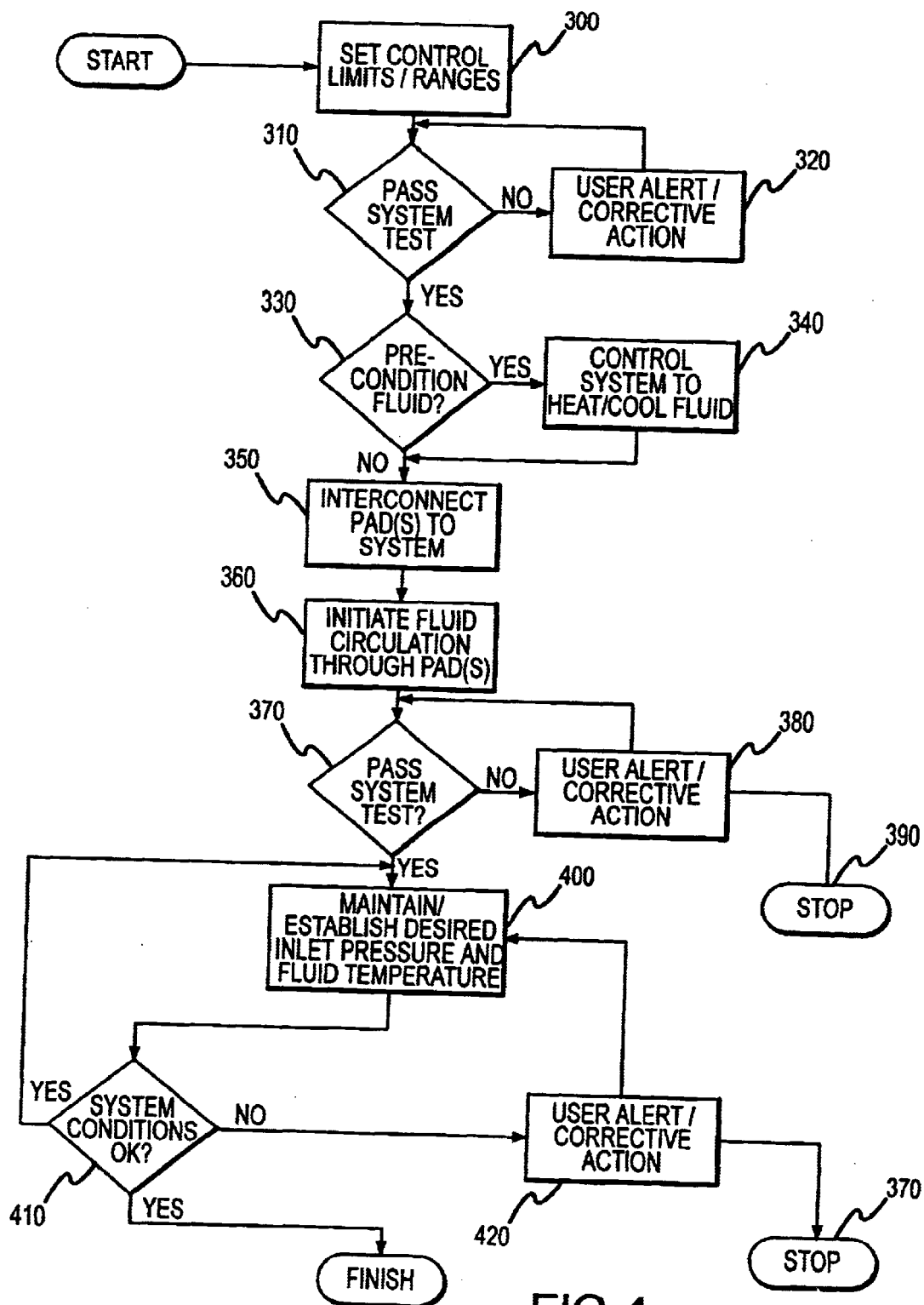
FIG. 4 is a process flow diagram of one embodiment of a patient temperature control method comprising the present invention.

Reference is now made to FIG. 4, which illustrates a process flow diagram of one embodiment of a patient temperature control method. Such method may be implemented in conjunction with operation of the system embodiment of FIGS. 1–3 and will be described in relation thereto to facilitate a better understanding of the various steps. It should be appreciated, however, that the methodology described here in below may be implemented in a variety of different system embodiments.

As shown in FIG. 4, the operation of system 10 may initially provide for the selective establishment of system control limits/ranges by a user (step 300). The setting of limits/ranges may be achieved by a user at input device 154 (e.g. via user-friendly prompting at displays 152). By way of example, the settable limits/ranges may include a targeted patient temperature, maximum/minimum patient temperatures, a target temperature for the circulated fluid, and maximum/minimum fluid temperatures.

Next, a system test may be completed (step 310) to confirm/calibrate key operational capabilities of the system 10. By way of example, such test may be automatically initiated upon completion of step 300 and/or otherwise may be selectively initiated pursuant to prompting at displays 152 and user input at input device 154. The system test may include any number of automated procedures initiated by processor 130 to confirm the operability of the various sensors, fluid handling devices, heat exchange devices and associated circuitry of system 10.

In particular, processor 130 may automatically transmit a test signal to temperature simulator 180 (e.g. comprising one or more resistors of known value(s)), thereby causing temperature simulator 180 to provide an analog signal input to comparator 166 for test purposes. For example, the test signal provided by processor 130 may cause temperature simulator 180 to provide an analog signal input to comparator 166 that exceeds a predetermined value (e.g. corresponding with a maximum temperature). Such signal should cause comparator 166 to transmit a signal to open switch 162 as well as a response signal to processor 130. In turn, processor 130 may monitor the response of switch 162 to confirm the operability of both comparator 166 and switch 162. The system test procedure may also include the provision of test signals from processor 130 to calibration simulator 182 (e.g. comprising one or more resistors). In turn, calibration simulator 182 may provide analog signals that are conditioned then employed by processor 130 to automatically calibrate the system 10 so that signals received from external sensors 210 during operation may be translated into accurate patient temperatures for display.

As illustrated in FIG. 4, if any of the system test procedures indicate a problem with system 10 (step 320), a user alert may be provided at user interface 150 (step 320). By way of example, visual alarms may be provided at displays 152. Additionally, and/or alternatively audible alarm signals may be provided at user interface 150. Upon the provision of the alarm output, a user may take appropriate corrective action to address the alarm condition. In this regard, the user interface 150 may display remedial instructions to a user and allow for user override in certain instances.

The process embodiment of FIG. 4 also provides for the optional preconditioning of fluid by system 10 (step 330). As previously noted, such preconditioning may entail the heating or cooling of fluid within system 10 prior to interconnection with one or more contact pad(s) 1. When time permits, such preconditioning may be desirable from the standpoints of both patient comfort and rapid patient temperature alteration. By way of example, the preconditioning step may be selectively initiated by a user via the input device 154.

Pursuant to the initialization of fluid preconditioning (step 330), various components of system 10 may be automatically and/or manually controlled (step 340). More particularly, and referring now to FIG. 5, bypass valve 92 of system 10 may be opened (step 500) via transmission of a control signal by processor 130. In turn, circulating pump 20 may be operated at a predetermined speed (step 510) pursuant to the transmission of control signals by processor 130. The opening of bypass valve 92 and operation of circulating pump 20 causes fluid within make-up reservoir 40 to flow through the bypass fluid line 54, through circulating pump 20, and back into the make-up reservoir 40 via circulating reservoir 30.

Figure 5:
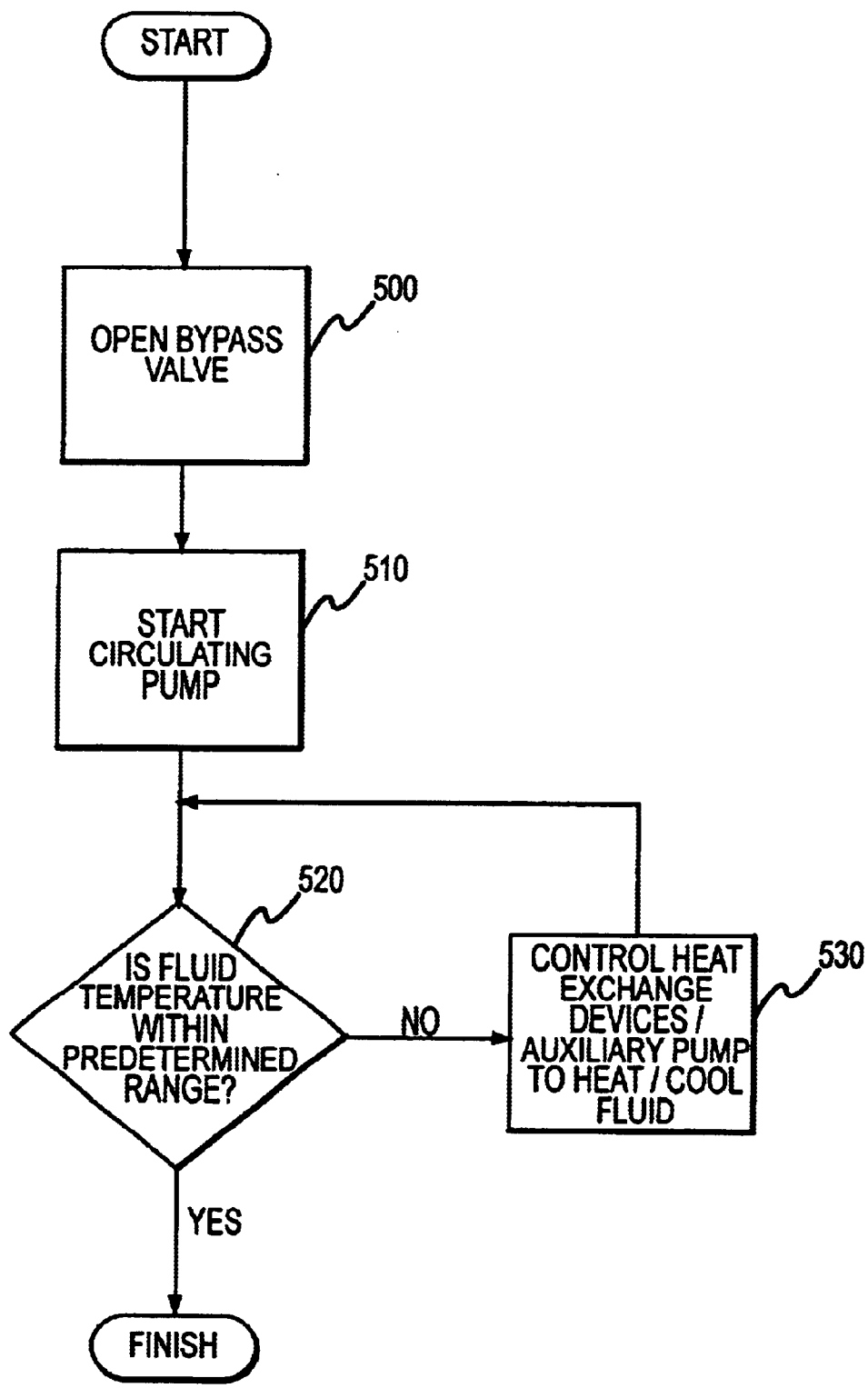
FIG. 5 is a process flow diagram for fluid preconditioning in the method embodiment of FIG. 4.

As indicated by FIG. 5, the fluid temperature may be sensed to determine if it is within a predetermined desired range (step 520). More particularly, temperature sensor 70 may be employed to sense the temperature of the fluid in circulating reservoir 30, wherein the sensed temperature signal is provided to processor 130 for comparison to a predetermined range. In the later regard, the predetermined range may be preset or otherwise established by a user in conjunction with set-up operations. In the event that the sensed temperature is not within the predetermined range, processor 130 may transmit control signals to heat exchange devices 62 or 64, and/or to auxiliary pump 68, to achieve the desired degree of fluid heating/cooling (step 530). As may be appreciated, the temperature sensing by sensor 70 and control of heat exchange devices 62, 64 and pump 68, by processor 130 may continue as needed to establish the desired fluid temperature.

Figure 6:
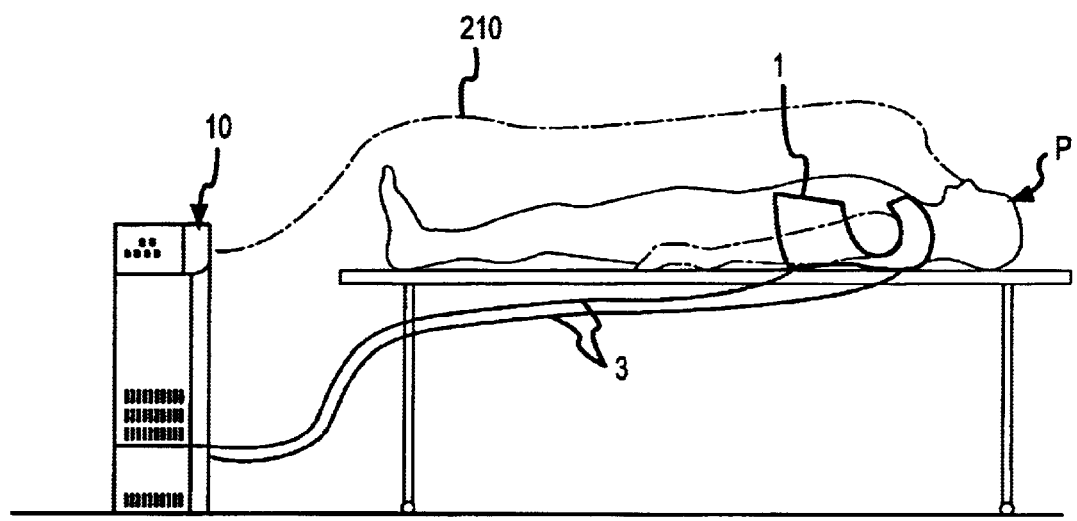
FIG. 6 is a diagrammatic view of an exemplary use of the present invention.
Figure 7:
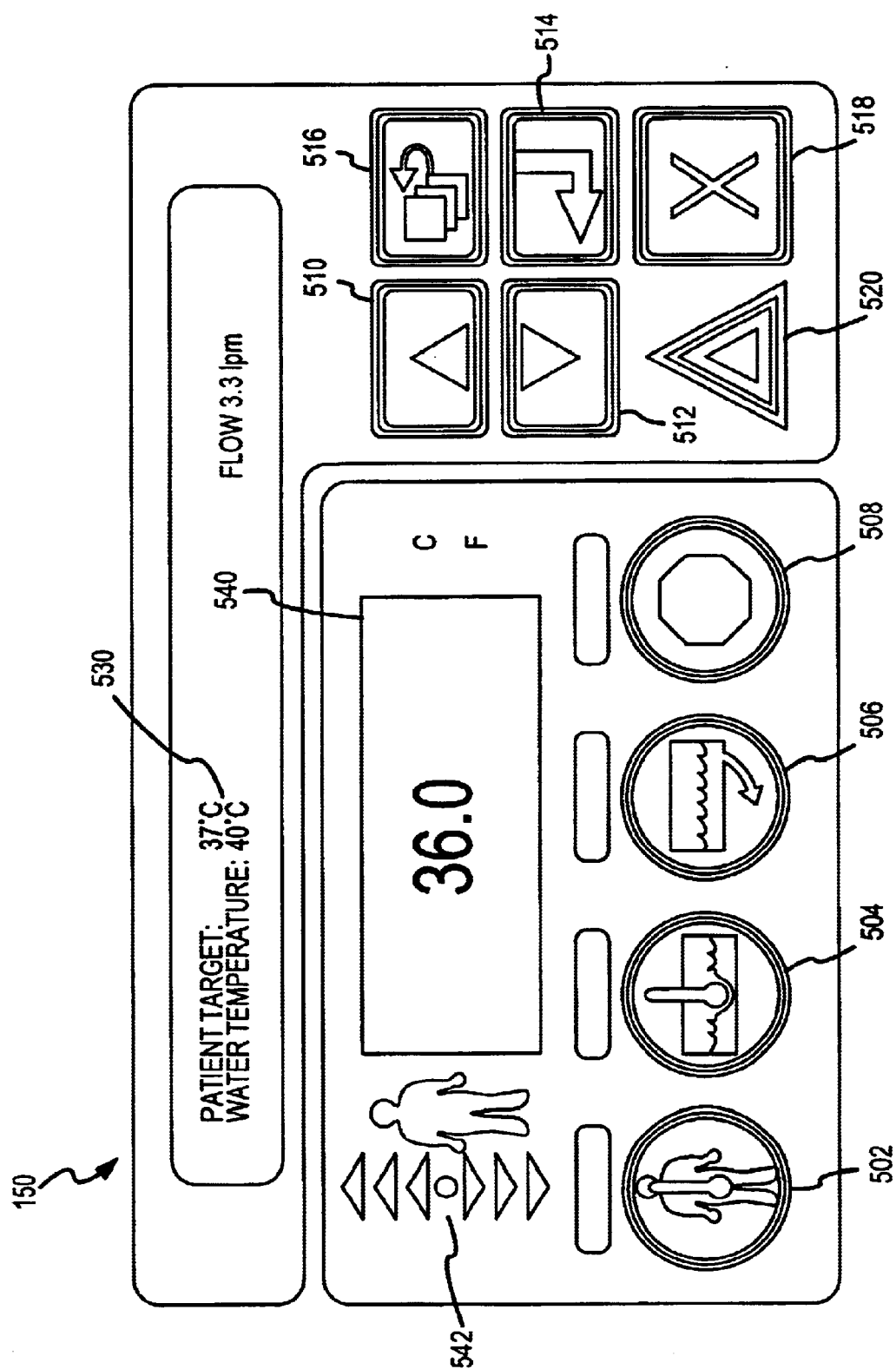
FIG. 7 is a front view of one embodiment of a user interface employable in conjunction with the present invention.

Returning now to FIG. 4, the initialization of actual patient heating/cooling entails the interconnection of one or more contact pads(s) 1 to the system 10 (step 350). In conjunction with such interconnection, system 10 may require a user to provide an appropriate control input at input device 154. After interconnection of the contact pad(s) 1, fluid circulation therethrough may be initiated (step 360). In this regard, appropriate user input may be required at input device 154, whereupon circulating pump 20 may be operated in accordance with a preset speed-setting algorithm. In conjunction with steps 350 and 360 noted above, the pad(s) 1 and patient should preferably be located above the system 10, as shown in FIG. 6.

At this point, further system testing may be provided (step 370). By way of primary example, processor 130 may utilize the signals provided by a flow meter 94 and/or pressure sensor 82, and the known operating speed of circulating pump 20, to determine if fluid is properly circulating through the system 10 and the interconnected pad(s) 1. More particularly, for a given operating speed of circulating pump 20 the pressure sensed by sensor 82 and the fluid flow measured by flow meter 94 should be predictable within a predetermined range under normal operating conditions. In the event that the signal received from flow meter 94 indicates a flow volume outside of the predetermined range, processor 130 may be provided to identify a condition of potential concern to a user as well as potential remedial action to be taken at user interface 150 (step 380). By way of example, a message may be provided at a display 152 to check for kinks in the tubing line 3 employed to interconnect pads 1 to the system 10. Further, processor 130 may be provided so that if system conditions fall outside of a predetermined range and/or are not corrected within a predetermined time, operation of circulating pump 20, heat exchange devices 62, 64 and/or auxiliary pump 68 is automatically terminated (step 190).

Assuming system 10 is operating within normal expected ranges, system 10 may be automatically controlled to provide the desired patient heating/cooling at interconnected pad(s) 1. In this regard, the inlet pressure at inlet port 120 may be maintained in a predetermined operating range and the temperature of the circulated fluid may be established to affect the desire heating/cooling of a patient through pads 1 (step 400). For purposes of maintaining the desired negative pressure in the interconnected pad(s) 1, processor 130 may utilize the sensed pressure signal provided by inlet pressure sensor 82 to control the speed of operating pump 20. For purposes of establishing the temperature of the circulating fluid the processor 130 may utilize one or both of the output signals from temperature sensors 72, 70 of system 10, as well as the sensed temperature signals provided by external temperature sensor(s) 210. Of note, it may be particularly advantageous to utilize all of such sensed temperature signals. More particularly, the utilization of all there signals allows for the computation of thermal exchange with a patient. In turn, control of the heat exchange devices may be set. In one arrangement, such setting may be provided utilizing the algorithm provided below:

$W = KQ(T_i - T_t) - M \, C \, dT_{avg}/dt$;

Where:
- W=Transfer of heat exchange devices 62, 64 and 66;
- K=Conversion of calories/minute to watts;
- Q=Water flow rate (e.g. measured by flow meter 94);
- $T_i$=Water inlet temperature (e.g. measured by sensor 72);
- $T_t$=Water target temperature (e.g. as set by a user);
- M=Mass of circulating water (e.g. as input to or determined by system 10);
- C=Heat capacity of water; and,
- $dT_{avg}/dt$=Rate of change of average circulating water temperature (e.g. as determined using measurements by sensor 70).

Returning now to FIG. 4, the output signals from sensors 70, 72, 74, 82 and 94 may be employed on a periodic basis to in sure system operation within preset acceptable ranges (step 410). In the event monitored operations are outside acceptable limits user alerts for corrective action may be provided (step 420), and if the condition of concern continues operations may be automatically terminated (step 390).

Reference is now made to FIG. 6, which illustrates one embodiment of a user interface 150. Such interface 150 will be described to in relation to an exemplary application of various features of the system 10 described above. The user interface 150 comprises user operating keys 502–518, a message screen 530, and a patient temperature display 540. The message screen 530 displays parameter settings, warnings, and alarms during operation.

If a patient temperature sensor 210 is utilized in a given procedure, display 540 provides the measured patient temperature. In one arrangement, display temperatures should range from 25° C. to 42° C. With a patient temperature sensor 210 in place, icon 542 indicates trends or changes in patient temperature. As shown, icon 542 may comprise a plurality of upward oriented and downward oriented arrows with a circle disposed therebetween. An illuminated upward yellow arrow indicates that a patient's temperature is rising. An illuminated downward yellow arrow indicates that a patient's temperature is falling. The higher or the lower the illuminated arrow, the faster the temperature is changing. When only the yellow circle is lit, the temperature of the patient is substantially constant.

Four main modes of automated operation of system 10 can be set utilizing keys 502–508:
1. "Patient Temperature Control Mode"—set by pushing key 502;
2. "Water Temperature Control Mode"—set by pushing key 504;
3. "Purge Mode"—set by pushing key 506; and,
4. "Stop Mode"—set by pushing key 508.

Additional information about a particular mode and modification of corresponding parameter settings may be achieved by pressing the "Up Arrow" key 510 or "Down Arrow" key 512 while in the given mode, as will be further described.

In the Patient Temperature Control Mode system 10 automatically functions to monitor and control a patient's temperature to a set target temperature. Water will be cooled or warmed as needed and pumped through the pad(s) 1 to achieve the target temperature. In one arrangement, patient temperature can be controlled and monitored between 33° C. and 37° C. When activated, a yellow indicator light over the key 502 is illuminated. A water flow rate will be displayed on the message screen 530 in liters per minute (i.e. "1 pm").

In the Water Temperature Control Mode system 10 automatically functions to flow temperature-controlled water through the pad(s) 1. Water is controlled to a specific target temperature set by the operator. In one arrangement, the target water temperature and can be set between 4° C. and 42° C. When activated, a yellow indicator light over key 504 is illuminated. Unless an alarm condition occurs, water temperature and flow rate will be displayed in the message screen 530 when this mode is active.

In the Purge Mode system 10 automatically functions to empty water from the pad(s) 1. When the mode is activated a yellow light over key 506 is illuminated. A message (e.g. "Purging Water") will be displayed on the message display screen 530 when this mode is active. When pad(s) 1 have been emptied, the system 10 may be provided to automatically return to Stop Mode.

Pressing the Stop Mode key 508 at any time will stop any of the three other modes (i.e. Patient Temperature Control, Water Temperature Control Mode, or Purge Modes). When activated, the yellow light over the Stop Mode key 508 is illuminated. Any other mode can be activated from Stop Mode by pressing the corresponding mode key.

A variety of system settings and other information may be accessed from menus and information listings displayed at message screen 530 in the Stop Mode, Water Temperature Control Mode, and Patient Treatment Mode, including e.g.:

1. Set patient target temperature;
2. Set water target temperature;
3. Measured water level;
4. Set maximum/minimum water temperatures;
5. Set high and low patient temperature warning settings; and,
6. Other setup parameters (e.g. data output intervals).

As may be appreciated, the noted settings may be changed for each procedure. The system 10 may be provided so that once the system 10 has been turned off, settings return to default parameters. New default parameters can also be permanently saved if desired.

As noted above, the "Up Arrow" key 510 and "Down Arrow" key 512 allow users to scroll through menus and information listings on the message screen 530. Relatedly, the "Enter Key" 514 allows an operator to select and change parameter settings. For example, a given parameter listed on message screen 530 may be selected using arrow keys 510, 512, then the Enter key 514 may be pressed, causing the parameter to be displayed in a pronounced manner (e.g. brightened or varied color illumination). Next, the arrow keys 510, 512 may be utilized to increase or decrease the setting value. When the desired value is displayed, the user may then press the Enter key 514 again to establish the setting. The "Return to Main Menu Key" 516 will exit a given menu and return a user back to a main menu. The "Alarm/Alert" icon 520 is automatically illuminated upon detection of an alert or alarm condition. Pressing the "Cancel Key" 520 clears an alert or alarm.

Prior to use of the system 10, the reservoirs 30 and 40 should be filled with fluid, e.g. distilled or sterile water. To do so, the system 10 should be connected to a power source 160, e.g. via plug-in to an appropriate power supply outlet. After being turned on, the system 10 may be provided to conduct a brief self-check and enter the Stop Mode. The yellow light over the Stop Mode key 508 will be illuminated. Using the "Down Arrow" key 512, a user may scroll through the menu until the display reads "WATER LEVEL "XX" Uses—Press Enter to Fill". A user may then connect a fill tube into one of the inlet connectors on the block manifold 5. The other end of the fill tube may be placed into a water container. The Enter key 514 may then be pressed to cause system 10 to start filling and automatically stop when it is complete. The system 10 will then return the Stop Mode.

The filling process can be interrupted at any time by pressing the Stop Mode key 508; however, the reservoirs 30, 40 may not be adequately filled for the maximum number of uses. To determine how many procedures may be run before refilling (e.g. assuming a design limit of a predetermined number of pads), a user may use the Up and Down Arrow keys 510, 512, to scroll through the menus until the message screen 530 displays the water level and number of uses left.

As noted, many parameters for controlling temperature with the system 10 may be changed and/or customized and saved for future use. Prior to using the system 10 for a given patient, a user may determine which settings will be used. All parameters will return to default setting unless new settings are saved.

Treatment parameters can be accessed while the Stop Mode key 508 is lit. A user may press the Up Arrow key 510 or Down Arrow key 512 to scroll through the various menu options. In one arrangement, the default settings and ranges of options may be set as follows:

User Selected Operational Settings:

| Parameter | Default | Options |
|---|---|---|
| Data Output Interval | 1 minute | Off, 5 seconds to 10 minutes Intervals from 5 to 60 seconds - 5 seconds Intervals from 1 to 10 minutes - 1 minute |
| Data Output Format | Compacted | Compacted or Detailed |

User Selected Treatment Modes:

| Parameter | Default | Range | Incremental Changes |
|---|---|---|---|
| Patient Target Temperature | 37° C. | 33.0° C. to 37.0° C. | 0.1° C. increments |
| Water Target Temperature | 37° C. | 4.0° C. to 42.0° C. | 1.0° C. increments |
| Maximum Water Temperature | 42° C. | 32.0° C. to 42.0° C. | 1.0° C. increments |
| Minimum Water Temperature | 4° C. | 4.0° C. to 32° C. | 1.0° C. increments |

User Adjustable Alerts:

| Parameter | Default | Range | Incremental Changes |
|---|---|---|---|
| Patient High Temperature Alert | 42.0° C. | 25.1° C. to 42.0° C. | 0.1° C. |
| Patient Low Temperature Alert | 25.0° C. | 25.0° C. to 41.9° C. | 0.1° C. |

| Parameter | Default | Incremental Changes |
|---|---|---|
| Chiller Connected for Cooling | No | Yes or No |

To change any of the default settings, from the Stop Mode a user may utilize the following procedure:

1. Use the Up Arrow key 510 and Down Arrow key 512 to access a setting that will be displayed on the message screen 530.
2. Press the Enter key 514 and the parameter that can be modified will be highlighted.
3. Press the Up Arrow key 510 or Down Arrow key 512 to reach the desired settings. Press the Enter key 514 to save.
4. To change additional settings, continue to scroll through the menu, pressing the Up Arrow key 510 or Down Arrow key 512 to access the appropriate screens.
5. Repeat the procedure to highlight, select, and save the displayed parameters.
6. The newly configured parameters will remain throughout a given procedure until the system 10 is turned off.

All customized parameters can be permanently saved or until a user decides to change them. To save the newly set parameters as defaults settings a user may utilize the following procedure:

1. Scroll through the menu screen until a "SETUP" screen is displayed.

2. Press the Enter key 514 and scroll through the menu until "Save Current Settings" is displayed.

3. Press the Enter key 514 to save the settings.

Then, a temperature sensor 210 may be placed in the patient and connected to the system 10. Thereafter, the patient's temperature can be monitored and controlled.

To continue patient treatment, a user may press the Stop Mode key 508 and confirm all of the parameters are programmed to the desired setting using menus provided when the Stop Mode key 508 is activated, as described above. The following settings are of primary note:

1. Patient target temperature: determines the temperature set-point for the patient. Temperature set range may be limited to 33° C. to 37° C.

2. Maximum water temperature: allows a user to determine the highest water temperature that will circulate through the pads during Patient Treatment Mode.

3. Patient temperature high limit or low limit alerts: allows a user to determine patient temperatures at which the system 10 should provide an alert.

Next, a user may press the Patient Temperature Control Mode key 502. Thereafter, the message screen 530 will show the set patient target temperature, the current water temperature and the current water flow rate in the system 10. For certain procedures or before a temperature sensor 210 is placed, a warming or cooling cycle can be initiated without controlling temperature. The Water Temperature Control Mode can be used to circulate temperature-controlled water without automatically controlling patient temperature. This mode may be used whether or not a temperature probe has been placed. To do so, a user may access a water target temperature screen by pressing the Up Arrow key 510 or Down Arrow key 512 while in either the Stop Mode or Water Temperature Control Mode. Then a user may adjust the water temperature to a desired setting as follows:

1. Press the Up Arrow key 510 or Down Arrow key 512 until the following appears in message screen 530: "Water Target Temperature 37° C., Enter to Change".

2. If a new water target temperature is desired, press the Enter key 514 to highlight the temperature.

3. Press the Up Arrow key 510 or Down Arrow key 512 until the desired temperature is displayed. Press the Enter key 514. Changes can be made in increments of 1.0° C./F between 4.0° C. and 42° C.

Once the water target temperature is set, and mode key 502 is pressed, the system will begin to adjust the water temperature to the desired setting. Flow rate will be shown on the message screen 530. Flow rate may vary depending on the size of the patient, the style of the pads used, and the number of pads that are applied.

As noted, system 10 may incorporate features into the system 10 that allow a user to pre-program certain alarms, including:

1. Patient temperature alerts; and,

2. Water temperature alerts.

In particular, the system 10 may provide a default alarm that will warn when a patient temperature exceeds a set level, provided water temperature continues to rise or stays above that set level. There is also a default alarm that will warn a user when a patient temperature falls below a set level, provided water temperature continues to decrease or stays below that set level.

The high and low patient set temperature alerts can be established by a user as follows:

1. While in Stop Mode, scroll through the menu using the Up Arrow key 510 or Down Arrow key 512 until the screen displays, "Patient Temperature High Alert 42° C., Enter to Change" or "Patient Temperature Low Alert 25.0° C., Enter to Change".

2. Press the Enter key and select the new temperature by using the Up Arrow key 510 or Down Arrow key 512. The high temperature range may be provided for adjustment between 25.1° C. and 52.0° C. in 0.1° C. increments. The low temperature range may be provided for adjustment between 25.0° C. and 51.9° C. in 0.1° C. increments.

3. Press the Enter key to save.

As may be appreciated, numerous additional alerts and alarms may be provided.

More generally in that regard, it should be noted that the foregoing description is strictly for the purpose of facilitating an understanding of the invention and is not otherwise intended to limit the scope thereof, as defined by the claims which follow.

What is claimed is:

1. A patient temperature control system, comprising:

a heat exchanger for one of heating and cooling a fluid;

a circulating pump for circulating said fluid first through said heat exchanger and second through at least one interconnectable contact pad, said circulating pump having an inlet side interconnectable with an outlet port of said at least one interconnectable contact pad, wherein operation of said circulating pump establishes a negative pressure in said at least one contact pad;

a pressure sensor fluidly interconnected between said inlet side of said circulating pump and said interconnectable outlet port of said at least one interconnectable contact pad, wherein said pressure sensor provides an output pressure signal employable to control said circulating pump;

a fluid reservoir, fluidly interconnectable with an inlet port of said at least one contact pad, for containing a portion of said fluid; and, a controller for utilizing said output pressure signal to provide control signals to said circulating pump, wherein said control signals control an operating speed of said circulating pump.

2. A system as recited in claim 1, wherein said output pressure signal is employable to control the operation of said circulating pump and thereby maintain said negative pressure within a predetermined range.

3. A system as recited in claim 2, wherein said output pressure signal is employable to control the operation of said circulating pump and thereby maintain said negative pressure within a predetermined range.

4. A system as recited in claim 1, wherein said fluid reservoir is internally maintained at substantially atmospheric pressure.

5. A system as recited in claim 4, further comprising:

a vent interconnected to said fluid reservoir to maintain said substantially atmospheric pressure within the fluid reservoir.

6. A system as recited in claim 1, wherein said controller generates said control signal utilizing said output pressure signal and predetermined information corresponding with a desired operating pressure range for said at least one interconnectable contact pad.

7. A system as recited in claim 1, further comprising:

a flow meter for measuring a flow rate of said fluid between an outlet side of said circulating pump and an inlet port of said at least one contact pad, wherein said flow meter provides an output flow signal; and, a user output device for providing an output in response to the identification of a predetermined relationship between said operating speed of said circulating pump and said output flow signal.

8. A system as recited in claim 7, wherein said output comprises remedial information.

9. A system as recited in claim 7, wherein each of said heat exchanger, fluid reservoir and flow meter are located downstream of said circulatory pump and upstream of said at least one interconnectable contact pad.

10. A patient temperature control method comprising:

operating a circulating pump to circulate a fluid through a heat exchanger and at least one fluidly interconnected contact pad said circulating pump having an inlet side interconnected with an outlet port of said at least one contact pad, wherein a negative pressure is established in said at least one contact pad;

sensing a pressure of said fluid between said inlet side of said circulating pump and said outlet port of said at least one contact pad and providing an output pressure signal in relation to said sensed pressure; and, utilizing said output pressure signal to provide a control signal to said circulating pump, wherein said control signal controls an operating speed of said pump.

11. A method as recited in claim 10, wherein said output pressure signal is employable in said operating step to maintain said negative pressure within a predetermined range.

12. A method as recited in claim 10, further comprising:

containing a portion of said fluid in a fluid reservoir; and maintaining said fluid reservoir internally at substantially atmospheric pressure.

13. A method as recited in claim 12, wherein said maintaining step comprises:

venting said fluid reservoir to maintain said substantially atmospheric pressure therewithin.

14. A method as recited in claim 10, wherein said utilizing step comprises:

utilizing said output pressure signal and predetermined information corresponding with a desired operating pressure range for said at least one contact pad.

15. A method as recited in claim 10, further comprising:

measuring a flow rate of said fluid between an outlet side of said circulating pump and an inlet port of said at least one contact pad.

16. A method as recited in claim 15, further comprising:

providing an output to a user in response to the identification of a predetermined relationship between said pump operating speed and said output flow signal.

17. A method as recited in claim 16, wherein said output comprises remedial information.

18. A patient temperature control system, comprising:

heat exchanger for one of heating and cooling a fluid;

a circulating pump for circulating said fluid first through said heat exchanger and second through at least one interconnectable contact pad, said circulating pump having an inlet side interconnectable with an outlet port of said at least one interconnectable contact pad, wherein operation of said circulating pump establishes a negative pressure and said at least one contact pad;

a pressure sensor fluidly interconnected between said inlet side or said circulating pump and said interconnectable outlet port of said at least one interconnectable contact pad, wherein said pressure sensor provides an output pressure signal employable to control an operating speed of said circulating pump;

a flow meter for measuring a flow rate of said fluid between an outlet side of said circulating pump and an inlet port of said at least one contact pad, wherein said flow meter provides a output flow signal; and, a user output device for providing an output in response to the identification of a predetermined relationship between an operation speed of said circulating pump and said output flow signal.

19. A system as recited in claim 18, further comprising:

a controller for utilizing said output pressure signal to provide control signals to said circulating pump, wherein said control signals control said operating speed of the circulating pump.

20. A system as recited in claim 19, further comprising:

a fluid reservoir, fluidly interconnectable with an inlet port of said at least one contact pad, for containing a portion of said fluid, wherein said fluid reservoir is internally maintained at substantially atmospheric pressure.

* * * * *

UNITED STATES PATENT AND TRADEMARK OFFICE
CERTIFICATE OF CORRECTION

PATENT NO. : 6,645,232 B2  Page 1 of 1
DATED : November 11, 2003
INVENTOR(S) : Carson It is certified that error appears in the above-identified patent and that said Letters Patent is hereby corrected as shown below:

<u>Title page,</u>
Item [56], References Cited, insert the following:
-- 5,609,571   3/1997    Buckberg et al.
   5,609,620   3/1997    Daily
   5,643,191   7/1997    Buckberg et al.
   5,645,531   7/1997    Thompson et al.
   5,702,358   12/1997   Witherspoon et al.
   5,730,720   3/1998    Sites et al.
   5,817,045   10/1998   Sever, Jr.
   5,957,137   9/1999    Dalke et al.
   5,957,879   9/1999    Roberts et al.
   5,997,816   12/1999   McIntosh et al.
   6,019,783   2/2000    Philips et al.
   6,042,559   3/2000    Dobak, III
   6,110,139   8/2000    Loubser
   6,254,626   7/2001    Dobak, III et al.
   6,261,312   7/2001    Dobak, III et al.
   3,744,555   7/1973    Fletcher et al. --

Signed and Sealed this

Twenty-fourth Day of February, 2004

JON W. DUDAS
*Acting Director of the United States Patent and Trademark Office*